United States Patent [19]
Lindemann et al.

[11] Patent Number: 4,765,320
[45] Date of Patent: Aug. 23, 1988

[54] DYNAMIC LOW PROFILE SPLINT

[75] Inventors: Peer Lindemann, West Bend; Robert R. Ungemach, Brown Deer, both of Wis.

[73] Assignee: Smith & Nephew Rolyan, Inc., Menomonee Falls, Wis.

[21] Appl. No.: 48,088

[22] Filed: May 11, 1987

[51] Int. Cl.$^4$ ................................................ A61F 5/04
[52] U.S. Cl. .................................................... 128/87 A
[58] Field of Search ................ 128/26, 77, 84 C, 87 A

[56] References Cited

U.S. PATENT DOCUMENTS

| | | | |
|---|---|---|---|
| 818,332 | 4/1906 | Anson | 128/26 |
| 867,981 | 10/1907 | Krizek | 128/26 |
| 2,553,277 | 5/1951 | Robinson et al. | 128/26 |
| 3,707,963 | 1/1973 | Keropian | 128/77 |
| 3,714,940 | 2/1973 | Palmer | 128/87 A |
| 3,788,307 | 1/1974 | Kistner | 128/77 |
| 3,815,587 | 6/1974 | Guerrant | 128/87 A |
| 4,602,620 | 7/1986 | Marx | 128/84 C |

FOREIGN PATENT DOCUMENTS 299882  8/1917  Fed. Rep. of Germany ........ 128/77

Primary Examiner—Robert A. Hafer
Assistant Examiner—Michael Brown
Attorney, Agent, or Firm—Ira Milton Jones

[57] ABSTRACT

A dynamic low profile splint to support an injured hand and allow movement of the fingers and assist extension of the fingers to overcome stiffness and immobility in the hand.

10 Claims, 2 Drawing Sheets

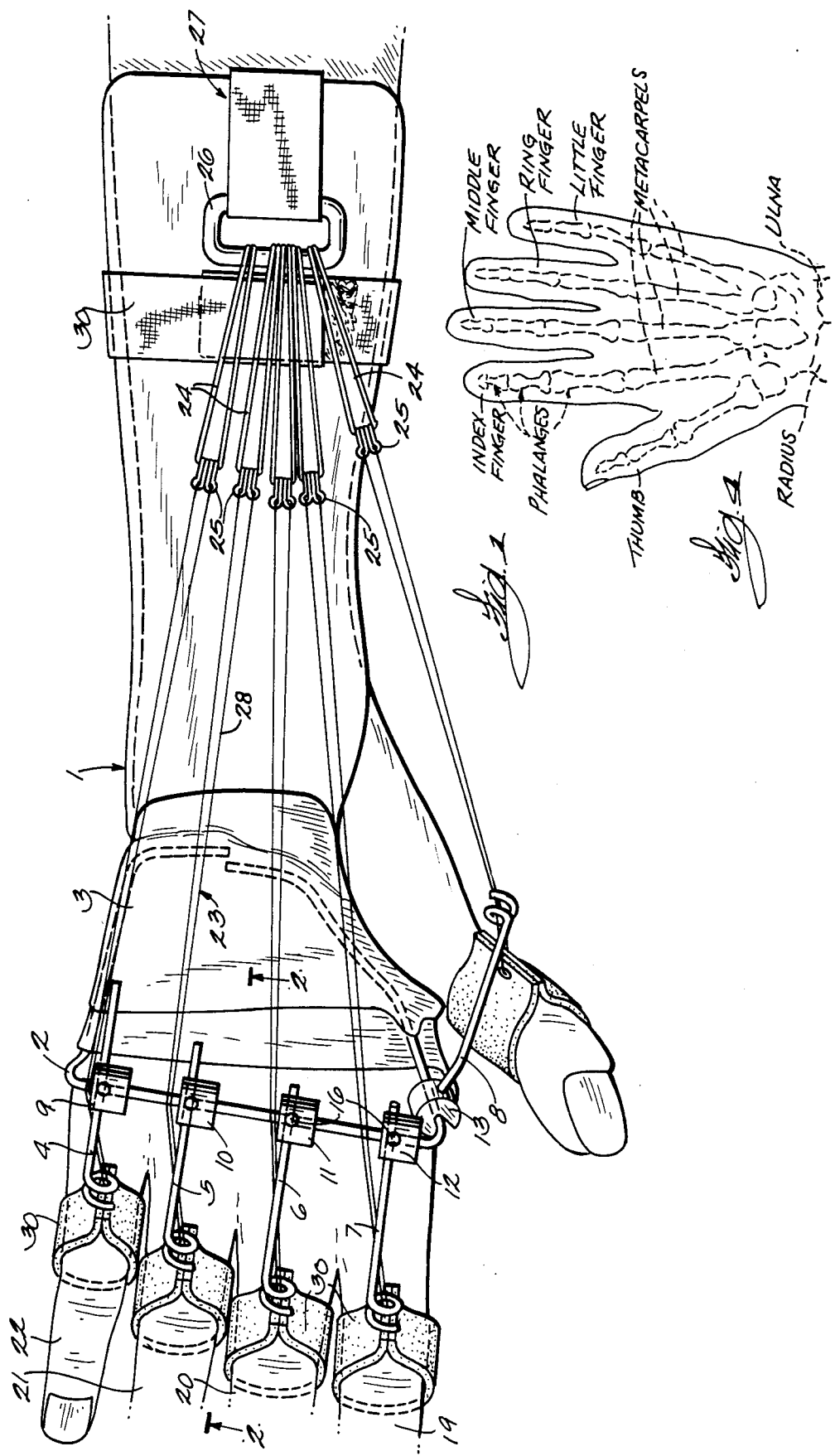

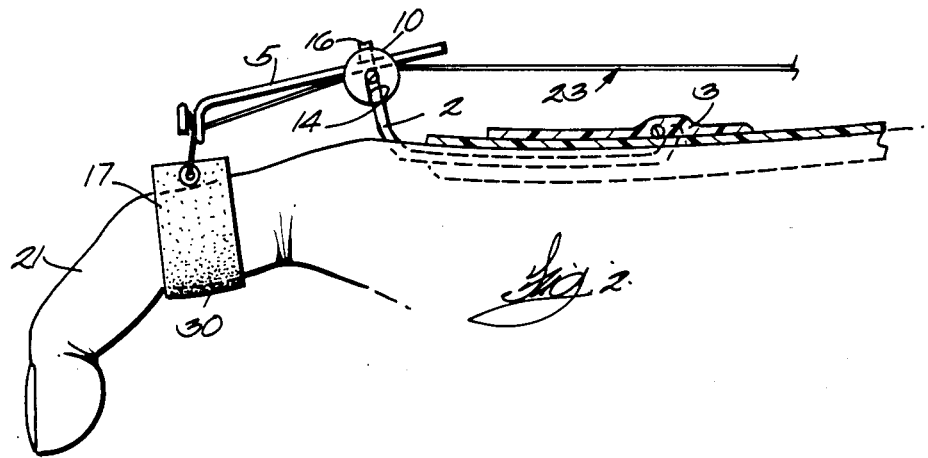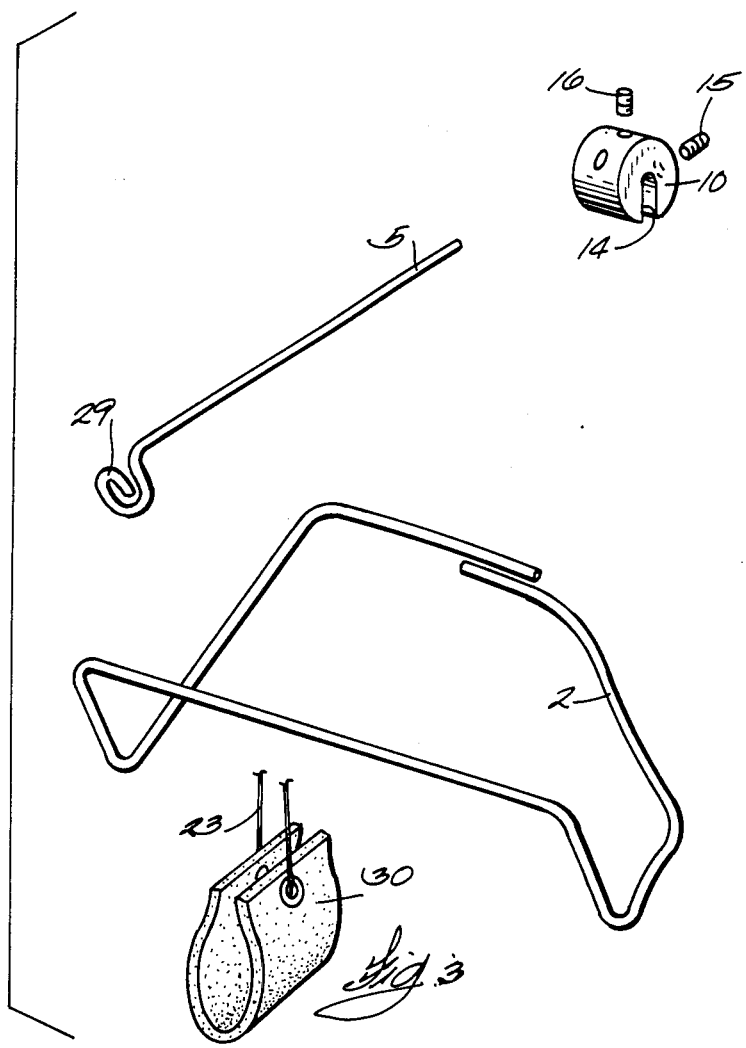

DYNAMIC LOW PROFILE SPLINT

This invention relates to hand splinting and, more particularly, to a dynamic and low profile splint having an adjustable outrigger to vary the tension and the direction of the force applied to the finger to overcome stiffness and immobility due to injury or due to the hand remaining in an immobile position over a period of time caused by the injury.

The human hand consists of a large number of bones and, obviously, a large number of joints joining these bones. It is essential that the hand is able to operate properly in order to function in all its intricate capacities.

In splinting a hand, one of the major goals of the occupational therapist is to help the hand function as independently as possible. When splinting, the hand should be maintained in a functional position, if possible. Whenever possible the patient should be able to perform normal tasks with the splint in place.

The joints of the hand are prone to adhesions and stiffness following immobilization, even for a short period of time, because of the hand's complex anatomy. Accordingly, dynamic splinting is a well accepted means in maintaining or gaining joint motion in the injured hand. Dynamic splinting allows movement of the joints and a more normal healing of the tissues in the hand.

Splinting of the hand should also consider the convenience as well as aesthetics. Low profile dynamic splinting avoids the bulkiness of prominent outriggers and and provides a convenience for the patient to pass the splint through a coat sleeve, if necessary.

The Keropian patent U.S. Pat. No. 3,707,963, shows an articulated handbrace in which wrist motion is permitted in the splint. A handpiece and a forearmpiece are pivotally connected by a plurality of articulating joints to allow movement of the wrist when the splint is in place.

The patent is directed to a means of allowing the wrist to flex and proving a means for conditioning the muscles and joints in the wrist to provide a more normal healing.

The applicant's invention is directed primarily to a low profile dynamic splint which provides for motion of the fingers while the splint is on the hand. A slight force is applied to each finger to allow the finger to flex and extend in the splint. The splint is designed to provide a low amplitude of force over a prolonged period of time to influence the synthesis of new tissue. The muscles of the hand producing a flexion are usually stronger than those which extend the fingers in the hand. Consequently, when an injury is incurred, the fingers tend to contract and a means for extending the fingers is necessary for normal healing. Applicant's splint provides such a device in which a low amplitude force is applied to each finger over a prolonged period to allow normal synthesis of the tissues.

Accordingly, it is believed that applicant's invention is distinguisable over the Keropian patent in that the device is designed for injury to the fingers, as compared to the flexible type of dynamic articulated handbrace of the Keropian patent.

It is an object of this invention to provide a dynamic low profile splint for a hand.

It is another object of this invention to provide a dynamic low profile splint having adjustable tension and adjustable means for varying the direction of the applied force on the fingers of a hand.

It is a further objection of this invention to provide a dynamic low profile splint with a forearmpiece constructed of low temperature thermal plastic to mold the forearmpiece to the contour of a forearm, and an outrigger which has adjustable means to vary the force and direction of the force applied to the fingers on the hand for providing normal healing.

The objects of this invention are accomplished through a forearmpiece molded to embrace the forearm with a comfort fit. The forearmpiece is preferably molded of a low temperature moldable plastic material which can be fitted to the wrist without any pressure points causing discomfort to the patient. The outrigger has a low profile and a pulley system or rigging which can be adjusted to change the direction of force to flex the fingers through finger pads or loops on the end of the rigging. A continued light force is applied to the fingers to cause them to restore the muscle and tendons to their original condition.

FIG. 1 is a plan view of a low profile dynamic splint;

FIG. 2 is a side section view of a portion of the low profile dynamic splint taken on line II—II of FIG. 1, showing the forearmpiece, outrigger and rigging for applying the force to the finger loop.

FIG. 3 is an exploded view of the outrigger and finger loop and rigging.

FIG. 4 illustrates the bones, joints and general anatomy of a hand and wrist.

Referring to the drawings, FIG. 4 illustrates generally the anatomy of a hand. The hand includes a thumb, an index finger, a middle finger, a ring finger and a little finger. The hand consists of a substantial number of bones articulated by joints connecting the bones. Because of the large number of joints and the complexity of the hand, immobility tends to cause stiffness, even for short periods of time. Because of the complex anatomy of the hand, it is necessary that a splint be made to accommodate flexing and extension of the fingers and movement of the hand as much as possible while it is splinted.

FIG. 1 illustrates a hand in a dynamic low profile spint. The forearmpiece 1 is preferably formed of a low temperature plastic moldable material which can be easily molded to fit the wrist and the hand. This permits custom fitting of the forearmpiece with ease and provides comfort for the patient. The outrigger frame 2 is fitted as an integral part with the forearmpiece by fitting it to the surface of the forearmpiece. A cap 3 of low temperature thermoplastic is then fitted over the frame which bonds readily to the forearmpiece to form an integral structure between these three components. The low height of the outrigger frame 2 above the forearmpiece keeps a low profile, as indicated in FIG. 2.

The frame 2 provides a mounting structure for the rigging guides 4, 5, 6, 7 and 8, each carried on a fastening clamp 9, 10, 11, 12 and 13, respectively. Each fastening clamp is provided with a slot 14 to receive the frame 2 and a set screw 15 to lock the fastening clamp in rigid position on the frame. Similarly a set screw 16 is provided to lock the rigging guide in position.

The rigging guide can be adjustably extended or withdrawn to provide the desired direction of force on the finger. The set screw 15 can also be loosened to adjust the position of the rigging guide by rotating the fastening clamp on the frame 2.

As viewed in FIG. 2, it will be seen that rotation of the fastening clamp 5 will allow greater or lesser movement of the finger as assisted by the loop 17. Adjustment of the rigging guide 5 axially changes the direction of the force on the finger as desired by the therapist.

A rigging is provided for each of the fingers, including the thumb 18, index finger 19, middle finger 20, ring finger 21 and little finger 22. The rigging 23, as shown in FIG. 2 as well as FIG. 1, consists essentially of an elastic band 24 which is fastened by means of a hook 25 to the strand 28. The band 24 is fastened in a ring 26 of the strap 27, which is bonded to the forearmpiece 1.

The strand 28 extends around the frame 2 which operates as a pulley and then extends through a loop 29 which directs the force to the finger loop 30.

The finger loop 30 is constructed of a material such as leather which has a softness for carrying the finger, but has sufficient stiffness so that it does not deform too much. It provides a soft resting place for the finger as the force assists extension of the finger by the rigging.

Each of the five riggings operate in the same manner and the adjustment of tension is essentially provided by the length of the elastic band connected to the strand. Positioning of the rigging guide also can affect the tension on the strand as well as the direction of the force transmitted to the loop.

The operation of the low profile splint is designed primarily to extend the fingers and the interphalangeal joints. The forearmpiece is constructed in such a manner that the wrist is held in a static position. The fingers, however, are in a position so that they can extend when assisted by the forces from the riggings, as shown.

Although the dynamic low profile splint is designed to extend the fingers, it is understood that a similar arrangement might be constructed whereby other movement of the fingers might be provided. Primarily, the muscles and tendons of the hand tend to cause a flexion of the fingers and cause them to bend in a contracted position, as shown in FIG. 2. This is primarily because the muscles tending to cause the fingers to flex in this direction, are substantially greater than the muscles and tendons which tend to extend the fingers to a straight position. Accordingly, the device is provided so that the fingers can be extended. The finger loops may be positioned on any of the phalanges to extend the full length of the fingers, if so desired. For the purpose of illustration, only one position is shown, and this is primarily where a dynamic splint of this type would be used.

The direction of the force can be adjusted by rotating the fastening clamp 10 on its axis by adjusting the set screw 15. Extension of the rigging guide 5 is adjusted by the set screw 16. Axial movement of the rigging guide vaires the position of force applied to the finger.

Preferably the strands are constructed of Nylon or a meterial which glides easily over the frame or the rigging guide.

Providing a continuous tension of low amplitude force on each of the strands over a prolonged period of time will influence the synthesis of the new tissue formed in the finger. It is preferable not to place too great a strain on the finger, nor to immediately straighten the finger to its normally extended position. A slight force will cause the finger to straighten and the muscles, tendons and nerves to stretch to their normal condition, and the new tissue will heal in the process.

The elastic bands 24 may be replaced with one of greater or lesser length. Preferably a substantial length is preferred because tension in the strand remains substantially constant even though there is some movement if the elastic band is fairly long. A shorter band would cause a more rapid change in tension if the strand moves as the finger straightens.

The forearmpiece 1 is provided with a strap 30 and preferably a Velcro fastening material, which will fasten the forearmpiece and maintain it in position. More than one strap may be used, if desired.

The embodiment of the invention in which an exclusive privilege or property is claimed are defined as follows:

1. A dynamic low profile splint for a hand, comprising:
   a forearmpiece for embracing an arm and hand;
   a low profile outrigger formed integral with said forearmpiece, including a frame carrying an elongated bendable rigging guide to provide lateral guide adjustment,
   said rigging guide having a pulley means for guiding a rigging;
   a fastening clamp adjustably fastening said rigging guide for rotational and axial movement on said frame to vary the force and direction of force in the longitudinal and vertical direction applied by the rigging on a finger loop;
   a rigging connected to said forearmpiece and extending over said frame and outrigger guide;
   at least one finger loop on said rigging for engaging a finger on a hand;
   a pulley means on the outrigger,
   said pulley means and said rigging thereby providing an adjustable tensioning device to provide low amplitude of force over a period of time to influence the synthesis of tissue in the finger.

2. A dynamic low profile splint for a hand, comprising:
   a forearmpiece for embracing a forearm and hand;
   a low profile outrigger having a frame fastened integrally with said forearmpiece, including an elongated laterally adjustable rigging guide;
   a clamp fastener adjustably connecting said rigging guide for rotational and axial adjustment in the longitudinal and vertical direction on said outrigger;
   means fastening said outrigger to said forearmpiece;
   a rigging fastened to said forearmpiece and extending through said rigging guide;
   a finger loop on the end of said rigging for engaging a finger,
   said rigging thereby applying a force to said finger loop;
   said clamp fastener including adjustable means to rotatably and axially adjustably position said rigging guide and the direction of force on said finger loop and the degree of force applied to said finger loop.

3. A dynamic low profile splint for a hand, comprising:
   a forearmpiece of low temperature moldable material for embracing a forearm and a hand;
   a low profile outrigger including a frame integral with the forearmpiece;
   a pulley system on said outrigger including an elongated laterally adjustable rigging guide operating as a pulley for changing the direction and the force applied by a rigging;

a fastening clamp adjustable fastening said rigging guide on the outrigger for rotational and axial adjustment and selectively locking said rigging guide in a locked position;

means on said fastening clamp adjusting the rigging guide for varying the rigging direction vertically and longitudinally and the tension;

at least one rigging fastened to the forearmpiece having an elastic band for generating a force;

a strand connected to said elastic band and extending through said rigging guide;

a finger loop on the end of said strand for engaging a finger;

said outrigger thereby providing infinite adjustable tension and direction of said rigging force applied to the finger loop to vary the influence of synthesis in said finger.

4. A dynamic low profile splint as set forth in claim 1, wherein said fastening clamp defines a cylindrical sleeve having screw locking adjustments.

5. A dynamic low profile splint as set forth in claim 2, wherein said clamp fastener extends and retracts the rigging guide to vary the force applied to a finger loop.

6. A dynamic low profile splint as set forth in claim 2, wherein said clamp fastener includes means for rotating and axially adjusting said rigging guide on said frame to vary the direction of force applied to said finger loop and said finger loop can be positioned at any point along the length of the finger.

7. A dynamic low profile splint as set forth in claim 1, wherein said outrigger includes a wire frame and a wire rigging guide.

8. A dynamic low profile splint as set forth in claim 1, wherein said forearmpiece includes a fastening strap for embracing a forearm.

9. A dynamic low profile splint as set forth in claim 2, wherein said claim fastener defines a cylindrical element with screw means to allow rotatable movement of the clamp fastener and axial movement of the rigging guide to adjust the force applied to said finger loop.

10. A dynamic low profile splint as set forth in claim 1, wherein said clamp fastener includes means to provide a slidable rigging guide with a rotatable clamp to vary the force on said finger loop.

* * * * *